United States Patent [19]

Suzuki et al.

[11] Patent Number: 5,157,453
[45] Date of Patent: Oct. 20, 1992

[54] LIQUID CONTENT DETECTING DEVICE FOR ALCOHOL REGULAR GASOLINE AND PREMIUM GASOLINE FUEL MIXTURE

[75] Inventors: Hiroyoshi Suzuki; Kenji Ogawa, both of Himeji, Japan

[73] Assignee: Mitsubishi Denki Kabushiki Kaisha, Tokyo, Japan

[21] Appl. No.: 727,682

[22] Filed: Jul. 10, 1991

[30] Foreign Application Priority Data

Aug. 3, 1990 [JP] Japan .................. 2-207280

[51] Int. Cl.⁵ .................................... G01N 21/41
[52] U.S. Cl. .................................... 356/128; 356/133
[58] Field of Search ............... 356/128, 133, 135, 136, 356/137; 250/227.14; 123/1 A, 494

[56] References Cited

U.S. PATENT DOCUMENTS 3,426,211  2/1969  Anderson .
5,015,091  5/1991  Suzuki et al. ............... 356/135

FOREIGN PATENT DOCUMENTS 129235  8/1983  Japan .

Primary Examiner—F. L. Evans
Attorney, Agent, or Firm—Sughrue, Mion, Zinn, Macpeak and Seas

[57] ABSTRACT

A liquid content detecting device is provided which can detect the contents of liquid components such as alcohol in a mixed fuel (both regular and premium gasolines) with a high degree of preciseness at all times over the entire operating temperature range in which the device is used. A refractive index sensor senses the refractive index of a liquid mixture which includes N kinds of liquid components. A liquid-kine identifying means identifies the kind of each of the liquid components. A temperature sensor senses the temperature of the liquid mixture. A liquid content calculator stores a temperature-dependent refractive index characteristic of various kinds of liquids including the liquid components in advance. The liquid content calculator is operable to select the temperature-dependent refractive index characteristic of each of the liquid components, and calculate the contents of the liquid components in the liquid mixture on the basis of the thus selected temperature-dependent refractive index characteristics of the liquid components and the refractive indexes of the liquid mixture, which are sensed by the refractive index sensor at (N−1) different temperatures.

6 Claims, 8 Drawing Sheets

5,157,453

LIQUID CONTENT DETECTING DEVICE FOR ALCOHOL REGULAR GASOLINE AND PREMIUM GASOLINE FUEL MIXTURE

BACKGROUND OF THE INVENTION

The present invention relates to a device for detecting a property of a liquid such as a fuel containing a plurality of liquid components in a contactless manner. More particularly, it relates to a device for detecting the contents of liquid components such as gasoline, alcohol, etc. contained in a fuel as used with automotive engines.

In recent years, a fuel comprising gasoline mixed with alcohol has become popular for automotive use in many countries including the United States of America, European countries, etc., for the purpose of reducing the consumption of petroleum.

If, however, such an alcohol-mixed fuel is used for engines suited to a gasoline fuel which forms an air fuel mixture having a stoichiometric air/fuel ratio for proper combustion, the air/fuel ratio of a mixture formed of the alcohol-mixed fuel becomes leaner than that with the gasoline fuel due to the fact that the stoichiometric air/fuel ratio is much lower with a fuel containing alcohol than with a gasoline fuel containing no alcohol. For this reason, the content of alcohol in an alcohol-mixed fuel is detected so that engine control elements such as a fuel injector and the like are controlled in accordance with the alcohol content thus detected to properly adjust the air/fuel ratio, ignition timing, etc.; so as to provide good combustion.

Now, a typical example of a conventional fuel property detecting device will be described below.

FIG. 6 shows the general arrangement of a fuel property detecting device disclosed in Japanese Utility Model Laid-Open No. 62-81064. In this figure, the conventional fuel property detecting device includes a refractive index sensor, which is generally designated by reference numeral 101, for sensing the refractive index of a liquid fuel in a contactless manner, a refractive index calculator 102 for calculating the refractive index of the fuel based on the output signal of the sensor 101, a temperature sensor 103 for sensing the temperature of the fuel in the refractive index sensor 101 and generating a corresponding output signal, and an alcohol content calculator 104 for calculating the content of an alcohol contained in the fuel.

As shown in detail in FIG. 6, the refractive index sensor 101 includes a casing 115 at opposite ends of which a light emitter 111 and a light receiver 113 are disposed in an opposed, face-to-face relation so that light 117 emitted from the light emitter 111 passes through a cylindrical light guide 112 towards the light receiver 113.

The casing 115 has a hollow interior in the form of a fuel passage 116, an inlet port 118 for introducing a liquid fuel into the fuel passage 116, and an outlet port 119 for discharging the fuel from the fuel passage 116 to the outside. Thus, a fuel enters the casing 115 from the inlet port 118, flows around the cylindrical light guide 112 in the flow passage 116, and exits the casing 115 from the outlet port 119.

The outer peripheral surface of the cylindrical light guide 112 is sealingly supported at its opposite ends by the opposite end walls of the casing 115 through a pair of annular seals 114 which serve to prevent the leakage of fuel from the interior of the casing 115 towards the outside through the outer periphery of the light guide 112 and the opposite end walls of the casing 115.

The refractive index calculator 102 is connected to the light emitter 111 and the light receiver 113 for calculating the refractive index of the fuel in the fuel passage 116 in the casing 115 based on the output signal from the light receiver 113 and generating a corresponding output signal to the alcohol content calculator 104. Specifically, the refractive index calculator 102 calculates the refractive index of the fuel on the basis of a change or difference between the amount of light emitted from the light emitter 111 and that received by the light receiver 113.

The temperature sensor 103 in the form of a thermistor is mounted on the casing 115 for sensing the temperature of the fuel in the fuel passage 116 in the casing 115 and generating a corresponding output signal to the alcohol content calculator 104.

Based on the output signal of the refractive index calculator 102 and the output signal of the temperature sensor 103, the alcohol content calculator 104 calculates the content of an alcohol contained in the fuel in the fuel passage 116.

FIG. 7 shows the output characteristic of the refractive index calculator 102, and FIG. 8 shows the relationship between the alcohol content and the refractive index at a temperature of 20° C. in which a fuel whose refractive index is to be detected comprises regular or premium gasoline and an alcohol in the form of methanol admixed thereto.

The operation of the above-described fuel property detecting device will be described below. As shown in FIG. 6, the light emitter 111 emits beams of light 117 into the cylindrical light guide 112 at a large conical angle, which are refracted at the interface or boundary surface between the fuel, whose refractive index is NDf, in the fuel passage 116 in the casing 115 and the outer peripheral surface of the cylindrical light guide 112, whose refractive index is NDr, at angles of refraction which depend on the angles of incidence of the respective light beams 117. Thus, part of the light 117 from the light emitter 111 is refracted at the boundary surface and enters the body of fuel in the fuel passage 116, whereas the remaining portion of the light 117 is reflected at the boundary surface into the interior of the cylindrical light guide 112 and received by the light receiver 113.

In this regard, the critical or minimum angle of incidence, at which the light beams 117 from the light emitter 111 incident to the boundary surface are totally reflected into the interior of the cylindrical light guide 112, is called the angle of total reflection $\theta r$, and there is the following relationship between the angle of total reflection $\theta r$ and the refractive indexes NDf, NDr of the fuel and the light guide 112:

$$\sin \theta r = NDf/NDr$$

Therefore, all the light beams 17 having angles of incidence greater than the angle of total reflection $\theta r$ are reflected at the boundary surface into the interior of the light guide 112 and received by the light receiver 113.

The refractive index NDf of the alcohol-mixed fuel varies in accordance with the content of alcohol Cm therein, so the angle of total reflection $\theta r$ accordingly changes with the alcohol content Cm. Thus, the amount of light received by the light receiver 113 changes in dependence upon the alcohol content Cm in the fuel.

For this reason, the light receiver 113 comprises an element such as a phototransistor which generates an electric current having a magnitude proportional to the amount of light received. The current thus generated is input to the refractive index calculator 102 where it is converted into a corresponding voltage which is proportional to the amount of light received by the light receiver 113.

Now, let us consider the case in which the fuel to be detected comprises a gasoline in the form of regular gasoline mixed with methanol, and the cylindrical light guide 112 is formed of an optical glass BK7 having a refractive index of 1.52. In this case, as clearly shown in FIG. 8, the angle of total reflection $\theta r$ of regular gasoline (i.e., a fuel comprising regular gasoline containing no methanol (MO)) at room temperature, which has a refractive index of about 1.42, is about 69 degrees, whereas that of methanol (i.e., a fuel comprising 100% methanol containing no gasoline (M100) at room temperature, which has a refractive index of 1.33, is 49 degrees. As seen from FIG. 8, the higher the alcohol content Cm in regular gasoline, the lesser the refractive index NDf of the alcohol-mixed fuel and hence the lesser the angle of total reflection $\theta r$ becomes. Therefore, as the alcohol content Cm in regular gasoline increases, beams of light 117 projected from the light emitter 111 at an increasing conical angle of projection can reach the light receiver 113, so the amount of light received by the light receiver 113 increases. As a result, the output VND of the refractive index calculator 102 decreases in inverse proportion to the increasing refractive index NDf of the fuel, as clearly seen from FIG. 7.

Since the alcohol content Cm in the fuel is inversely proportion to the refractive index NDf thereof, as shown in FIG. 8, the alcohol content calculator 104 calculates, based on the output VND of the refractive index calculator 102, the alcohol content Cm and generates a corresponding output signal. In this case, however, the refractive index ND of the fuel varies with its temperature, i.e., in inverse proportion to the temperature thereof. Accordingly, the temperature sensor 103 senses the temperature Tf of the alcohol-mixed fuel and generates a corresponding output to the alcohol content calculator 104 which modifies, on the basis of the fuel temperature Tf, the alcohol content Cm, which is previously calculated from the output VND of the refractive index sensor 2, to provide a temperature-compensated correct alcohol content VCm.

With the above-described conventional device, however, in the case of a mixed fuel comprising a plurality of kinds of gasoline admixed with an alcohol such as, for example, one consisting of regular gasoline, premium gasoline and an alcohol, there will be an error in the alcohol content VCm calculated in the above manner, which can become $\Delta Cm$ at the greatest, as shown in FIG. 8. This is because there is a difference in the refractive index between regular gasoline and premium gasoline.

In addition, there is a variation in the temperature dependency of the refractive indexes of various kinds of fuels or different fuel components, so it is extremely difficult to exactly detect the content of an alcohol or a liquid component in a fuel mixture over a variety of kinds of fuels.

As a consequence, in cases where a mixed fuel comprising regular gasoline and an alcohol is admixed with premium gasoline, it becomes almost impossible to properly control the engine by accurately adjusting the air/fuel ratio of a mixture supplied to the engine, ignition timing, the amount of fuel injection, and the like.

SUMMARY OF THE INVENTION

Accordingly, the present invention is intended to overcome the above-described problems encountered with the conventional fuel property detecting device.

It is an object of the invention to provide a novel and improved liquid content detecting device which can detect the contents of liquid components such as an alcohol in a mixed fuel with a high degree of preciseness at all times over the entire operating temperature range in which the device is used.

In order to achieve the above object, according to the present invention, there is provided a liquid content detecting apparatus comprising:

a refractive index sensor for sensing the refractive index of a liquid mixture which includes N kinds of liquid components;

liquid-kind identifying means for identifying the kind of each of the liquid components;

a temperature sensor for sensing the temperature of the liquid mixture; and a liquid content calculator for storing a temperature-dependent refractive index characteristic of various kinds of liquids including the liquid components in advance, the liquid content calculator being operable to select the temperature-dependent refractive index characteristics of each of the liquid components, and calculate the contents of the liquid components in the liquid mixture on the basis of the thus selected temperature-dependent refractive index characteristics of the liquid components and the refractive indexes of the liquid mixture, which are sensed by the refractive index sensor at $(N-1)$ different temperatures.

The above and other objects, features and advantages of the invention will become more readily apparent from the following detailed description of a few preferred embodiments of the invention taken in conjunction with the accompanying drawings.

BRIEF DESCRIPTION OF THE DRAWINGS

In the drawings, the same or corresponding parts are identified by the same symbols.

DESCRIPTION OF THE PREFERRED EMBODIMENTS

A few preferred embodiments of the present invention will now be described in detail while referring to the accompanying drawings. In the following, for the sake of simplification in the description, the present invention will be described as applied for detecting the content of fuel components in a fuel which is used in an automotive engine.

Figure 1:
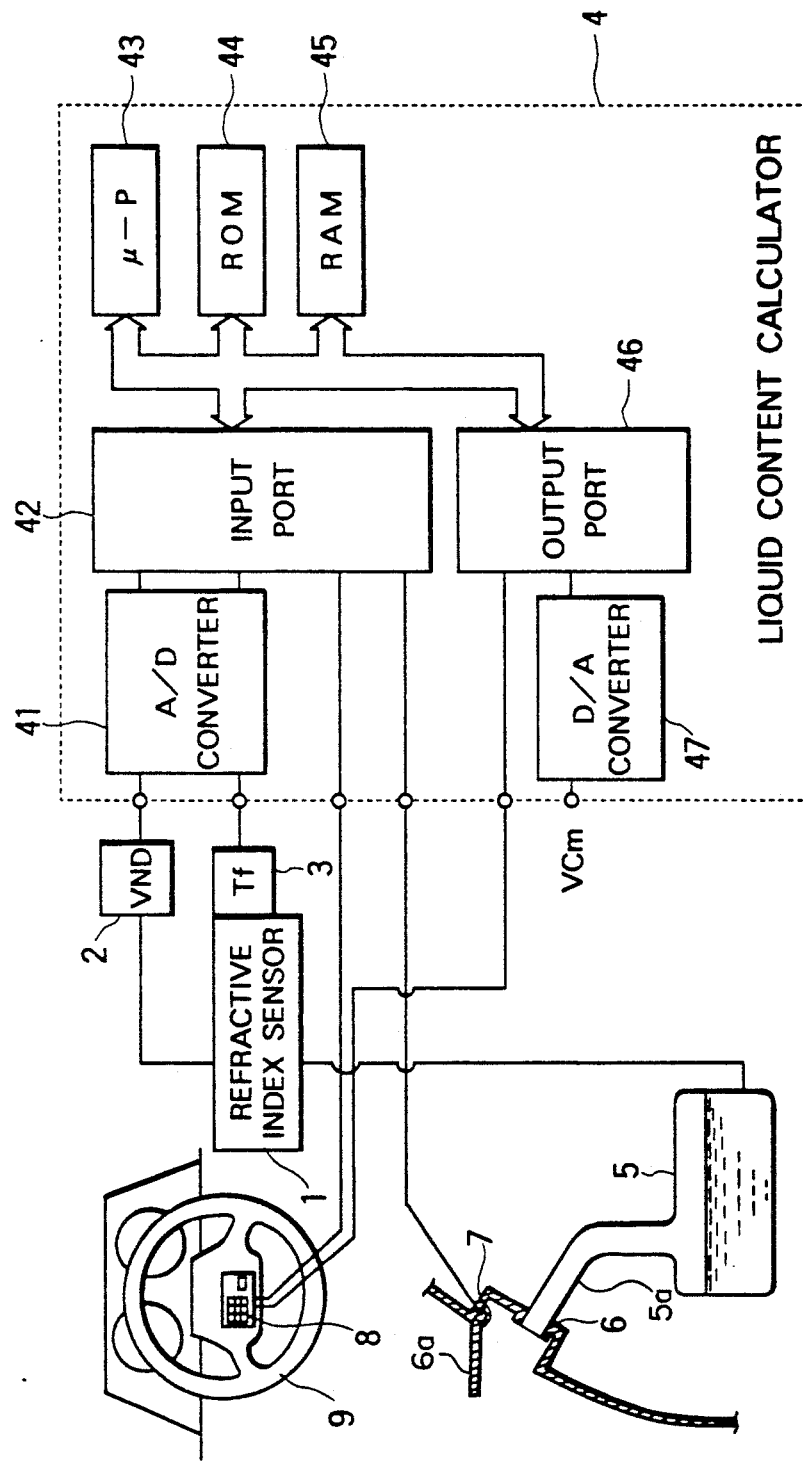
FIG. 1 is a block diagram showing the general construction of a liquid property detecting device in accordance with a first embodiment of the invention.
Figure 6:
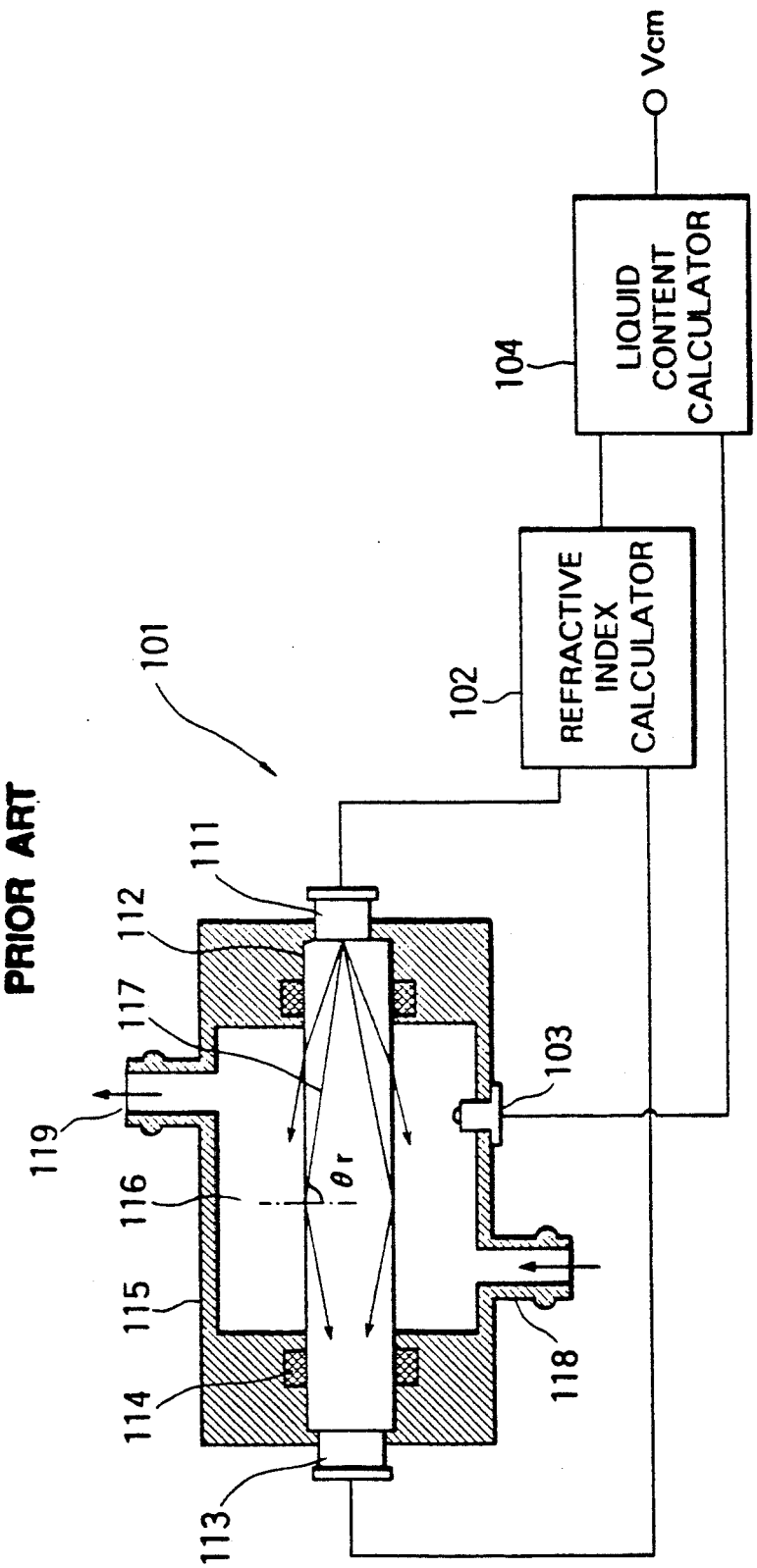
FIG. 6 is a black diagram showing an example of a conventional fuel content detecting device with a refractive index sensor illustrated in cross section.
Figure 7:
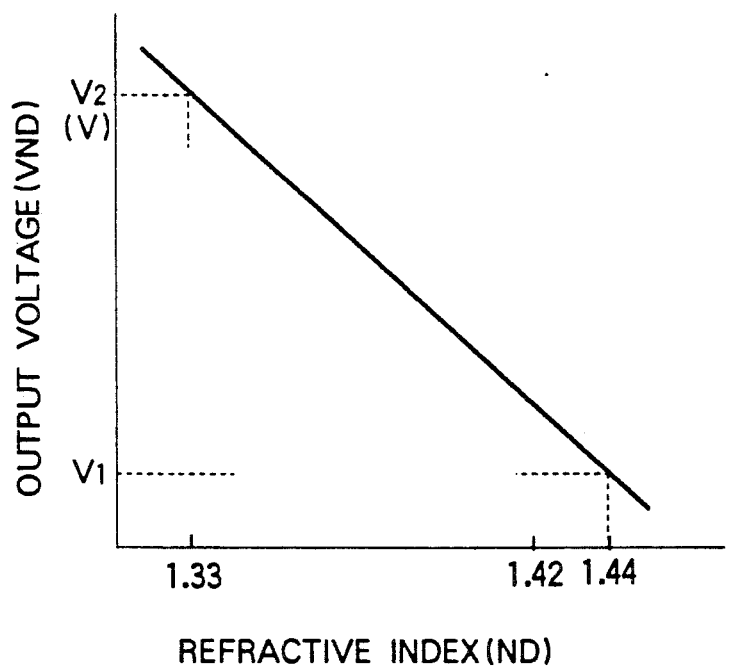
FIG. 7 is a diagram showing the output characteristic of a refractive index calculator of FIG. 6.
Figure 8:
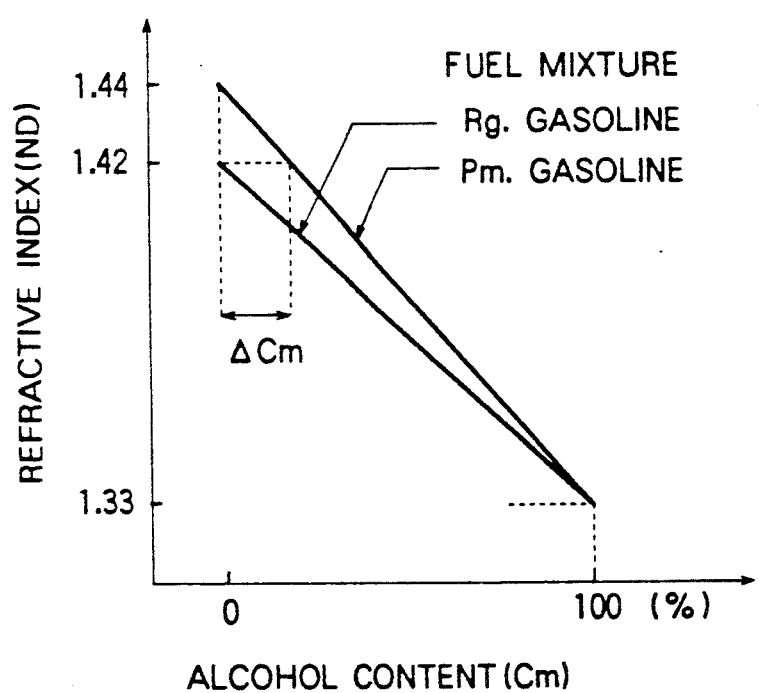
FIG. 8 is a diagram showing one example of the characteristic of the alcohol content versus the refractive index.

Referring first to FIG. 1, there is shown a liquid property detecting device constructed in accordance with a first embodiment of the invention. The device illustrated includes a refractive index sensor 1 for sensing the refractive index of a liquid which is, in this embodiment, in the form of a fuel and generating a corresponding output signal, a refractive index calculator 2 for calculating the refractive index of the liquid based on the output signal of the refractive index sensor 1 and generating a corresponding output signal in analog form, a temperature sensor 3 for sensing the temperature of the liquid in the refractive index sensor 1 and generating a corresponding output signal in analog form, and a liquid content calculator 4 for calculating the content of liquid components in the liquid based on the output signal from the refractive index calculator 2 and the output signal from the temperature sensor 3. In this embodiment, the refractive index sensor 1, the refractive index calculator 2 and the temperature sensor 3 may be the same as the elements 101 through 103, respectively, of FIG. 6, but the liquid content calculator 4 is different in construction and operation from the corresponding element 104 of FIG. 6.

Specifically, the liquid content calculator 4 includes an analog to digital (A/D) converter 41 for converting the output signal VND of the refractive index calculator 2 and the output signal Tf of the temperature sensor 3 from analog into digital form, an input port 42, a microprocessor 43, a read only memory (ROM) 44, a random access memory (RAM) 45, an output port 46 and a digital to analog (D/A) converter 47.

The output signal VND of the refractive index calculator 2 and the output signal Tf of the temperature sensor 3 are input to and A/D converter 41 where they are converted from analog into digital form. The digitized output signals of the A/D converter 41 are fed to the input port 42. The input port 42, the microprocessor 43, the ROM 44, the RAM 45 and the output port 46 are interconnected to each other through a data transmission bus for performing data or signal transmission therebetween.

The output signal from the output port 46 is converted from digital into analog form by the D/A converter 47 to provide an analog output signal VCm representative of the content of a liquid component such as an alcohol content in a liquid or fuel.

The device of FIG. 1 further includes a fuel supply system comprising a fuel tank 5 for storing a fuel which is combusted in the engine of a vehicle, a fuel supply port 6 formed at a portion of the vehicle body and connected to the fuel tank 5 through a fuel supply pipe 5a, and a fuel supply sensor 7 in the form of a switch attached to a lid 6a, which closes the fuel supply port 6, for sensing the opening and closing of the lid 6a and generating a corresponding output signal to the input port 42 of the liquid content calculator 4. Instead of sensing the operation of the lid 6a, the fuel supply sensor 7 may be formed so as to sense the opening and closing of a cap (not shown) which is attached to one end of the fuel supply pipe 5a.

A fuel-kind selector panel 8 is mounted on the top of a steering wheel 9 of the vehicle so that a driver can manipulate the panel 8 for providing information about the kind of a fuel supplied to the fuel tank 5 through the fuel supply port 6 as well as for indicating to the driver necessary information such as the content of a liquid such as an alcohol in a fuel from the output port 46 of the liquid content calculator 4.

Next, the operation of this embodiment will be described below. First, the refractive index sensor 1 senses the refractive index of a fuel supplied from the fuel tank 5 to the refractive index sensor 1 in the same manner as in the sensor 101 of FIG. 6 and generates a corresponding output signal to the refractive index calculator 2 which calculates the refractive index of the fuel based on the output signal of the refractive index sensor 1 and generates an output signal VND representative of the thus calculated refractive index in the same manner as in the calculator 102 of FIG. 6. The output signal VND of the refractive index calculator 2 in analog form is fed to the A/D converter 41 of the liquid content calculator 4 where it is converted into digital form and then read out by the microprocessor 43 through the input port 42.

On the other hand, the temperature sensor 3 senses the temperature of the fuel in the refractive index sensor 1 and generates a corresponding output signal Tf in analog form which is likewise fed to the A/D converter 41, converted there into digital form and read in by the microcomputer 43 through the input port 42.

Similarly, the output signal of the fuel supply switch 7 representative of the supply of a new fuel to the fuel tank 5 as well as an information signal from the fuel-kind selector panel 8 indicative of the kind of the new fuel supplied to the fuel tank 5 are input to the input port 42 of the liquid content calculator 4 and read out by the microcomputer 43. Contrarily, information such as the content of a liquid or fuel component in the fuel stored in the fuel tank 5, which is output from the microcomputer 43, is fed back to the fuel-kind selector panel 8 to provide a corresponding indication thereon.

Figure 2:
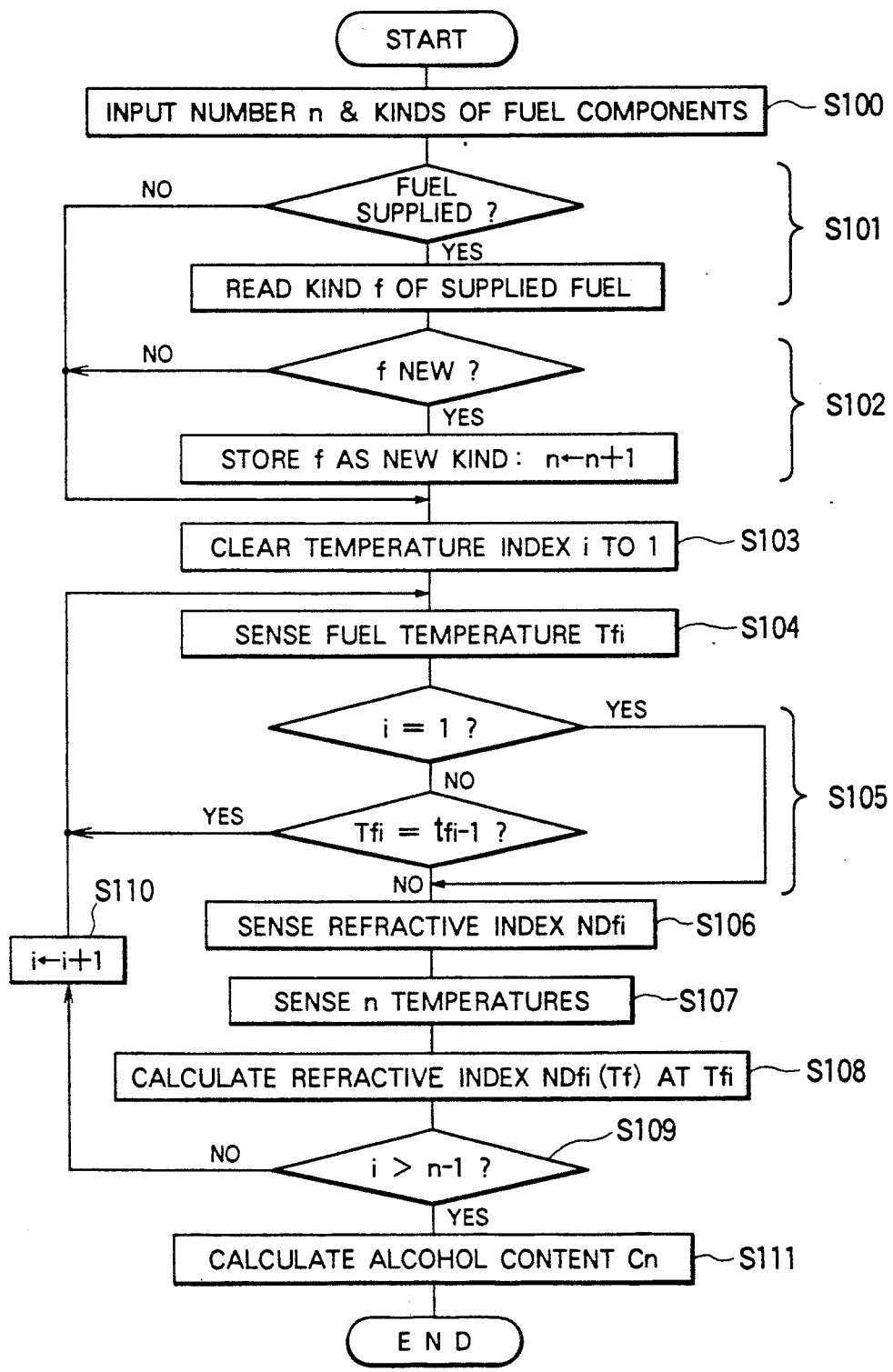
FIG. 2 is a flow chart showing the process of calculating an alcohol content performed by the device of FIG. 1.

On the basis of the various data fed to the input port 42, the microprocessor 43 performs operational calculations to provide the content of a liquid such as an alcohol contained in the fuel in the fuel tank 5 in accordance with the flow chart of FIG. 2.

In the following, one example of calculating such a liquid content in a fuel will be described with particular reference to FIG. 2. In this case, it is assumed that the fuel consists of regular gasoline and premium gasoline admixed with an alcohol in the form of methanol.

First in Step S100, the number n and kinds of fuel components, which are, in this example, regular gasoline, premium gasoline and methanol, are manually input from the fuel-kind selector panel 8 to the microprocessor 43 through the input port 42. Then in step S101, the output signal of the fuel supply switch 7 is read via the input port 42 into the microprocessor 43 where it is determined whether it is the time of supplying a fuel to the fuel tank 5. If so, the microprocessor 43 sends a corresponding signal to the fuel-kind selector panel 8 so as to reset the contents indicated or displayed thereon and at the same time request, through visual or voice instructions, the driver to input through the fuel-kind selector panel 8 information about the kind of a fuel component supplied to the fuel tank 5.

When the driver sets or inputs the kind f of a fuel component to be supplied by manipulating the fuel-kind selector panel 8, the process goes to Step S102 where it is determined whether the kind f of the fuel being supplied is a one that is already stored in the RAM 45. If not, the kind f of the fuel being supplied is determined to be a new one and stored in the RAM 45 as such.

More concretely, for example, suppose that the fuel already or previously stored in the fuel tank 5 before the supply of a new fuel consists of a mixture of regular gasoline and methanol, and that premium gasoline is supplied to the mixture. In this case, the supply of a new fuel in the form of premium gasoline is freshly stored in the RAM 45. If, however, premium gasoline has already been mixed into the fuel in the fuel tank 5, the Step S102 is unnecessary and skipped.

If in Steps S101 and S102 it is determined that the kinds of the fuel components contained in the fuel in the fuel tank 5 are regular gasoline, premium gasoline and methanol, then in Step S103, a fuel temperature sensing index i is cleared to "1". Thereafter in Step S104, the temperature $T_{fi}$ of the fuel mixture is read out, and in Step S105, it is determined whether the temperature $T_{fi}$ thus read is equal to a previously sensed temperature $T_{fi-1}$.

Figure 5:
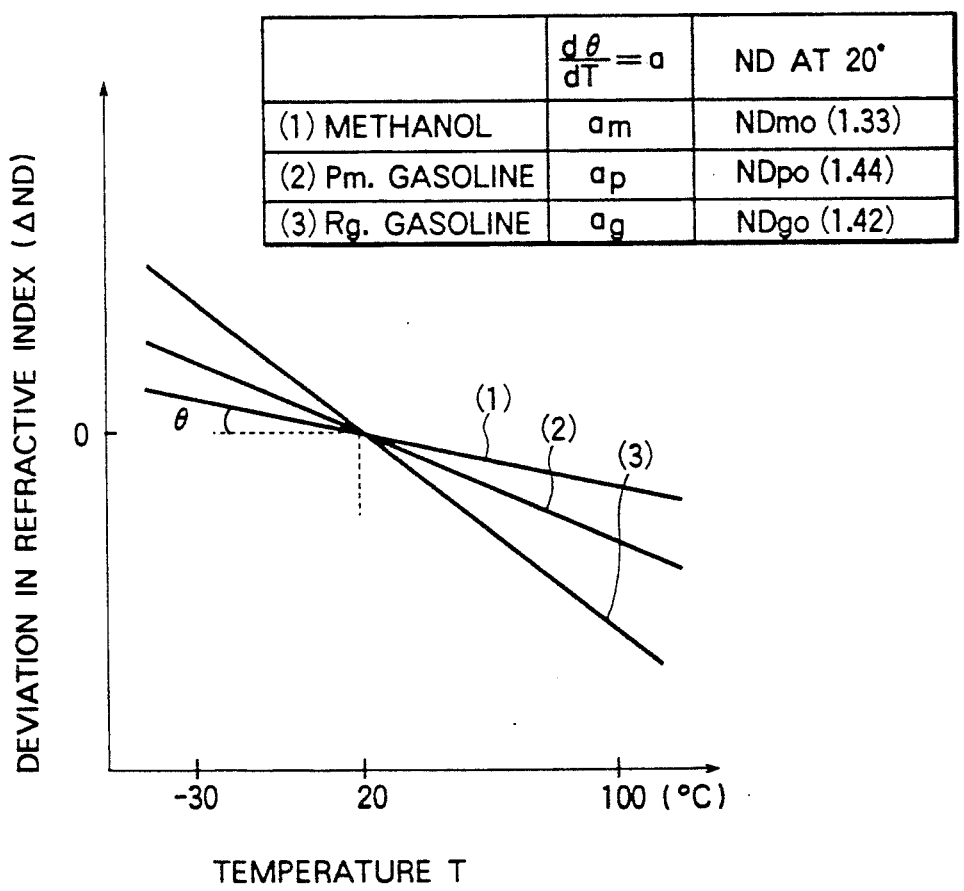
FIG. 5 is a diagram showing the relationship between the refractive index and the temperature of a fuel.

If the answer is positive in Step S105, the process returns to Step S104 to form a loop for reading out the fuel temperature $R_{fi}$ again. In this connection, only if the answer is negative in Step S105 (i.e., the most recent temperature $T_{fi}$ is not equal to the previous temperature $T_{fi-1}$), the process goes to Step S106 where the refractive index $ND_{Fi}$ of the fuel mixture is read out. Then in Step S107, amoung various temperature characteristics of fuel components which are stored in the ROM 44, the temperature characteristics of the three fuel components as previously set or selected (i.e., n=3) are read out. In Step S108, using the relationship between the refractive index and the temperature of the fuel components as illustrated in FIG. 5, the refractive indexes $ND_{gi}$, $ND_{pi}$ and $ND_{mi}$ of regualr gasoline, premium gasoline and methanol at a temperature of $T_{fi}$ are caluclated as follows:

$$ND_{gi} = ND_{go}\{1 - \alpha_g(T_{fi} - T_o)\}$$

$$ND_{pi} = ND_{po}\{1 - \alpha_p(T_{fi} - T_o)\}$$

$$TD_{mi} = ND_{mo}\{1 - \alpha_m(T_{fi} - T_o)\}$$

where $ND_{go}$, $ND_{po}$ and $ND_{mo}$ are the refractive indexes of regular gasoline, premium gasoline and methanol, respectively, at a predetermined reference temperature; and $\alpha_g$, $\alpha_p$ and $\alpha_m$ are the temperature coefficeints of the reflrative indexes of regular gasoline, premium gasoline and methanol, respectively. Accordingly, for the refractive index versus temperature characteristics, it is sufficient to store characteristic values at two points for each kind of fuel.

Subsequently, in Step S109, the fuel temperature sensing index i is compared with the number n of kinds of fuel components minus 1 (n−1) (in this example, n=3). If i<n−1, then in Step S110, the index i is incremented by "1" and the Steps S104 through S108 are repeatedly performed.

In this manner, the refractive index $ND_{f1}$ of the fuel mixture and the refractive indexes $ND_{g1}$, $ND_{p1}$ and $ND_{m1}$ at a temperature of $T_{f1}$ as well as those $ND_{f2}$, $ND_{g2}$, $ND_{p2}$ and $ND_{m2}$ at a temperature of $T_{f2}$ are determined.

Finally, in Step S111, on the basis of the values above determined, the alcohol content Cm in the fuel mixture is given as a solution of the following linear equation system having two unknown letters:

$$(ND_{m1} - ND_{g1})CM = (ND_{p1} - ND_{g1})CP = ND_{g1} = ND_{f1}$$

$$(ND_{m2} - ND_{g2})CM = (ND_{p2} - ND_{g2})Cp = ND_{g2} = ND_{f2}$$

where Cp is the content of premium gasoline in the fuel mixture.

The alcohol content Cm thus obtained is fed through the output port 46 to the D/A converter 47 where it is converted from digital into analog form to provide an analog output voltage CCm.

In this case, though not illustrated, if the content of premium gasoline Cp is also output from the liquid content calculator 4, much finer or more proper engine control such as, for example, ignition timing control can be carried out based on the premimum gasoline content Cp thus calculated.

As is apparent from the foregoing description, the contents of respective fuel components in a fuel mixture consisting of a total number n of various kinds of fuels can be calculated as a solution of a linear equation system having (n−1) unknown letters by measuring the refractive index of the fuel mixture at (n−1) points of temperatures.

Figure 3:
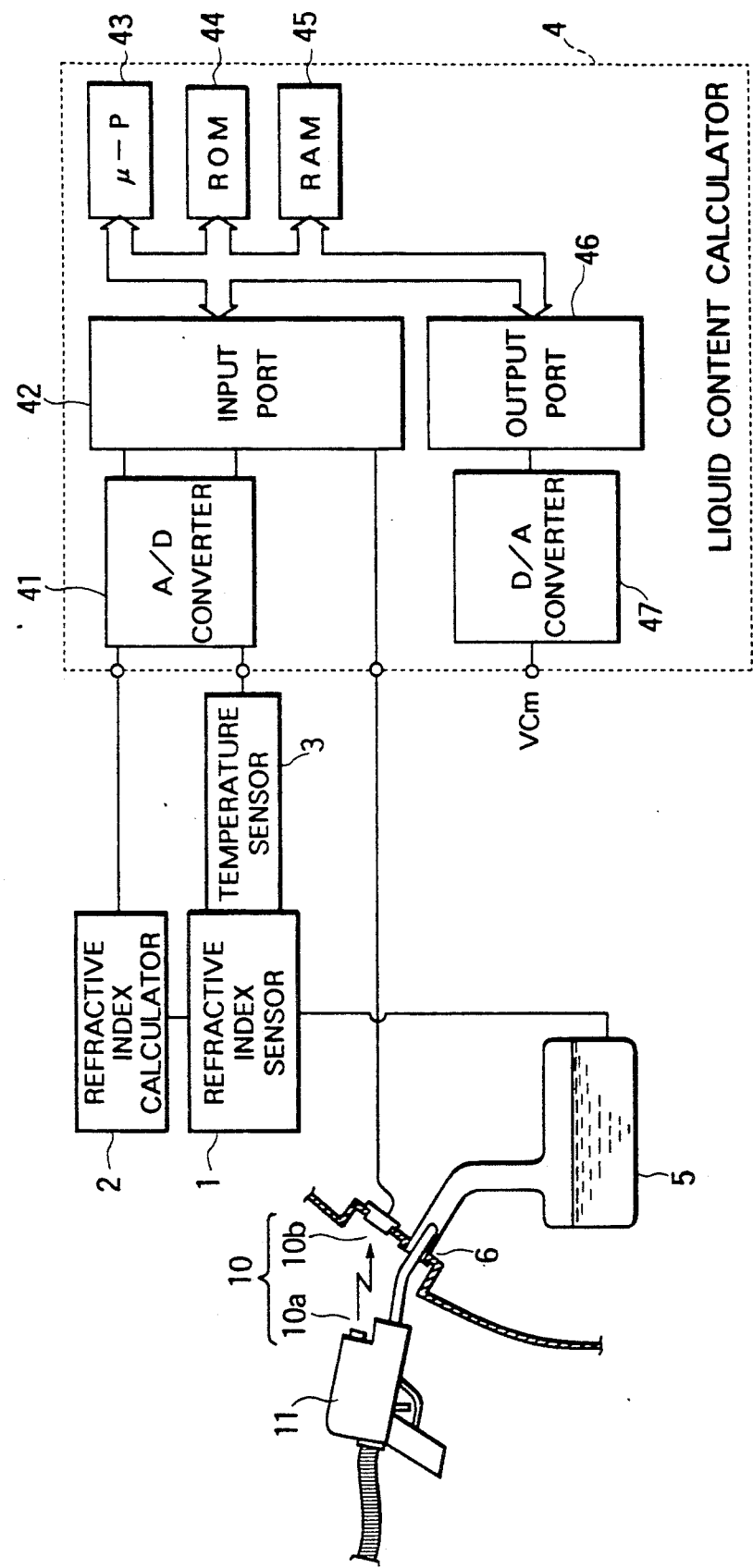
FIG. 3 is a view similar to FIG. 1, but showing another embodiment of the invention.

FIG. 3 shows another embodiment of the invention which is substantially similar to the previous embodiment of FIG. 1 exceopt for the prevision of a fuel-kind indentifying sensor to which includes a transmitter 10a mounted on a fuel supply nozzle 11, which is connected through a hose to a fuel supply (not shown), for transmitting a signal indicative of the kind of a fuel to be supplied from the nozzle 11, and a receiver 10b disposed near a fuel supply port 6 in the vehicle body for receiving the output signal from the transmitter 10a. When a fuel is supplied from the fuel supply nozzle 11 to the fuel supply port 6, the transmitter 10a transmits a fuel kind signal indicative of the kind of the fuel being supplied form the nozzle 11 towards the receiver 10b. Upon receipt of the fuel kind signal from the transmitter 10a, the receiver 10b sends it to a microprocessor 43 of a liquid content calculator 4 through an input port 42. Based on the fuel kind signal, the microcomputer 43 reads out the kind of the fuel being supplied to the fuel tank 5 as in Steps S101 and S102.

According to this embodiment, there is no need for the driver to manually set or input information about the kind of a fuel to be supplied. In addition, there is no fear of the driver's mistakenly inputting such information.

Figure 4:
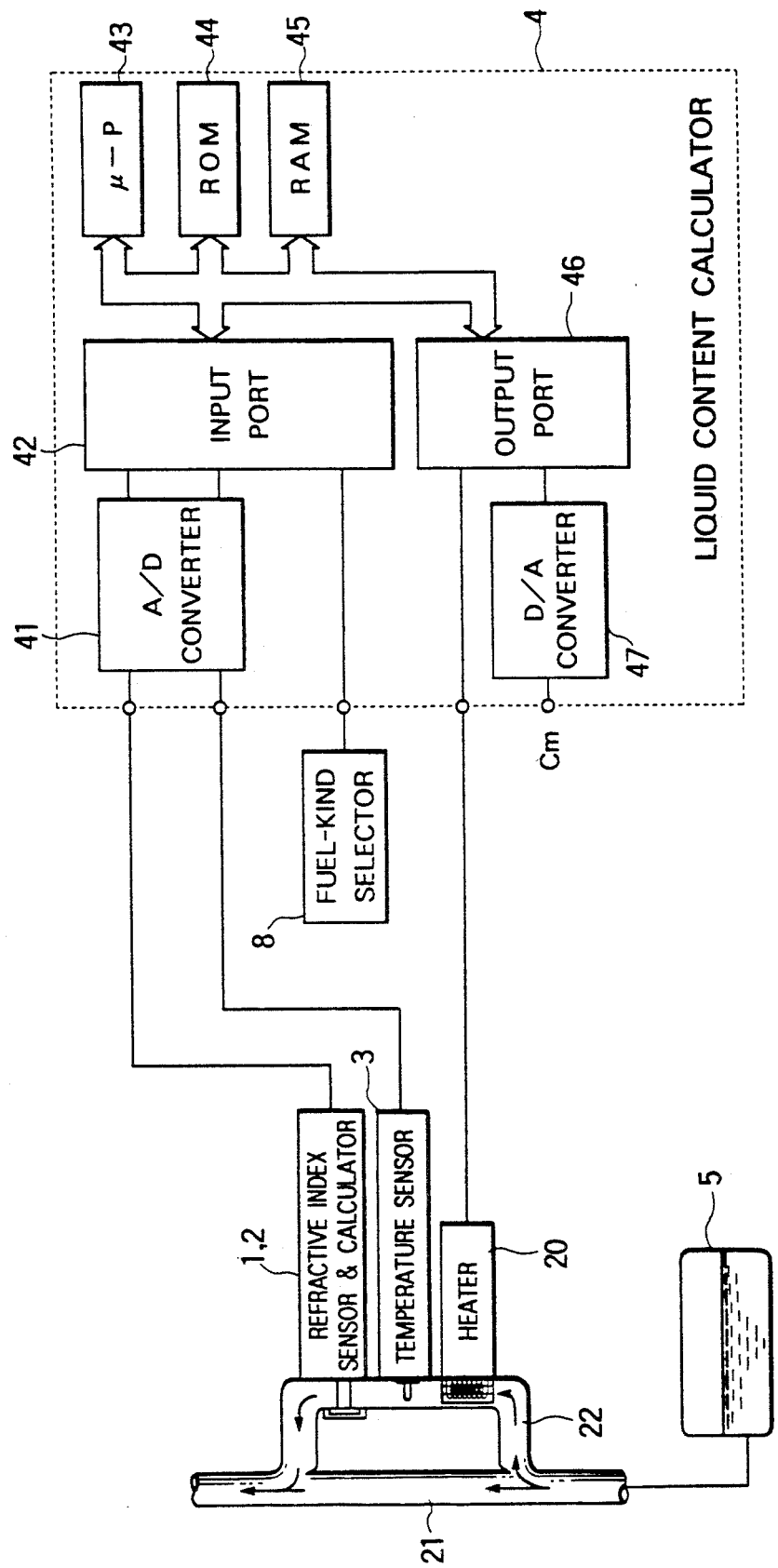
FIG. 4 is a view similar to FIG. 1, but showing a further embodiment of the invention.

FIG. 4 shows a further embodiment of the invention which is substantially similar to the embodiment of FIG. 1 except for the following features. Specifically, a fuel passage 21 connected to a fuel tank 5 is branched to form a bypass passage 22 of a reduced diameter on which there are installed a combination of a refractive index sensor 1 and a refractive index calculator 2, a temperature sensor 3, and a temperature changing means 20 for changing the temperature of a fuel whose refractive index is to be detected. The temperature changing means 20 is in the form of a heater disposed at a location upstream of the fuel temperature sensor 3. The heater 20 is controlled by a liquid content calculator 4 for heating the fuel in the bypass passage 22. In this embodiment, in cases where the temperature of the fuel in the fuel tank 5 remains substantially unchanged such as when the vehicle is cruising at a constant speed, the heater 20 can be operated under the control of the liquid content calculator 4 to heat the fuel in the bypass passage 22. Thus, the temperature of the fuel is positively changed so that the refractive index sensor 1 and the calculator 2 can detect and calculate the refractive index of the fuel at a plurality of different temperatures. As a result, even with a substantially constant fuel temperature, it becomes possible to precisely detect the contents of respective fuel components in the fuel mixture at any time irrespective of the running condition of the vehicle.

Although in the above embodiments, the liquid content calculator 4 calculates the contents of respective fuel components in a fuel mixture and generates corresponding outputs which are fed to an engine controller for proper engine control, it can be included in an engine control unit or the function of the calculator 4 can be performed by an engine control unit.

Moreover, in the above embodiments, the refractive index sensor 1 comprises a light sensitive type sensor, but it may be another type of sensor such as a light position sensitive sensor in which a light receiver receives beams of light, emitted from a light emitter through a light guide, at respective different locations in accordance with the different refractive indexes of various kinds of fuels.

Further, although in the above embodiments, the content of an alcohol contained in a fuel as used for automotive engines is detected, the present invention can of course be available generally for detecting the contents of other kinds of liquid components in a liquid.

What is claimed is:

1. A liquid content detecting apparatus for detecting the contents of liquid components in a liquid mixture, said apparatus comprising:

a refractive index sensor for sensing the refractive index of a liquid mixture which includes n kinds of liquid components;

liquid-kind identifying means for identifying the kind of each of the liquid components in the liquid mixture;

a temperature sensor for sensing the temperature of the liquid mixture; and a liquid content calculator for storing a temperature-dependent refractive index characteristic of various kinds of liquids including the liquid components in advance, said liquid content calculator being operatively coupled to the refractive index sensor, the liquid-kind identifying means and the temperature sensor, and responsive to output signals therefrom to select the temperature-dependent refractive index characteristic of each of the liquid components, and calculate the contents of the liquid components in the liquid mixture on the basis of the thus selected temperature-dependent refractive index characteristic of the liquid components and the refractive indexes of the liquid mixture, which are sensed by said refractive index sensor at $(n-1)$ different temperatures.

2. A liquid content detecting device according to claim 1, wherein said liquid-kind identifying means comprises a liquid-kind selector panel for manually inputting to said liquid content calculator information about the kinds of the liquid components.

3. A liquid content detecting device according to claim 2, wherein said liquid-kind selector panel provides an indication of the contents of the liquid components as calculated by said liquid content calculator.

4. A liquid content detecting device according to claim 1, wherein said liquid-kind identifying means comprises a sensor for sensing the kind of a liquid supplied to the liquid mixture and inputting the thus sensed kind of the liquid being supplied to said liquid content calculator.

5. A liquid content detecting device according to claim 1, further comprising means for changing the temperature of the liquid mixture so that said refractive index sensor can sense the refractive index of the liquid mixture at $(n-1)$ different temperatures.

6. A liquid content detecting device according to claim 5, wherein said means for changing the temperature of the liquid mixture comprises a heater for heating the liquid mixture.

* * * * *